(12) United States Patent
Gosset et al.

(10) Patent No.: US 12,144,733 B2
(45) Date of Patent: *Nov. 19, 2024

(54) IMPLANT FOR BONE AND CARTILAGE RECONSTRUCTION

(71) Applicant: Tornier SAS, Montbonnot-Saint-Martin (FR)

(72) Inventors: Irene Gosset, Le Touvet (FR); Robert J. Ball, West Olive, MI (US); Yves-Alain Ratron, Grenoble (FR)

(73) Assignee: TORNIER SAS, Montbonnot-Saint Martin (FR)

( * ) Notice: Subject to any disclaimer, the term of this patent is extended or adjusted under 35 U.S.C. 154(b) by 505 days.

This patent is subject to a terminal disclaimer.

(21) Appl. No.: 17/453,935

(22) Filed: Nov. 8, 2021

(65) Prior Publication Data

US 2022/0054272 A1 Feb. 24, 2022

Related U.S. Application Data

(63) Continuation of application No. 16/164,384, filed on Oct. 18, 2018, now Pat. No. 11,197,762, which is a
(Continued)

(30) Foreign Application Priority Data

Jul. 2, 2009 (FR) ...................................... 0954539

(51) Int. Cl.
*A61F 2/30* (2006.01)
*A61F 2/28* (2006.01)
*A61F 2/46* (2006.01)

(52) U.S. Cl.
CPC .. *A61F 2/30756* (2013.01); *A61F 2002/2817* (2013.01); *A61F 2002/2835* (2013.01);
(Continued)

(58) Field of Classification Search
CPC ............... A61F 2/30756; A61F 2/3603; A61F 2002/30757; A61F 2002/30759;
(Continued)

(56) References Cited

U.S. PATENT DOCUMENTS 5,171,276 A 12/1992 Caspari et al.
7,595,062 B2 9/2009 Pedrozo et al.
(Continued)

FOREIGN PATENT DOCUMENTS

| EP | 1366718 | 12/2003 |
|---|---|---|
| WO | WO 98/52498 | 11/1998 |
| WO | WO 2007/007106 | 1/2007 |

OTHER PUBLICATIONS

International Search Report issued in PCT/EP2010051539, mailed Apr. 28, 2010, 4 pages.

*Primary Examiner* — Marcia L Watkins
(74) *Attorney, Agent, or Firm* — DUANE MORRIS LLP

(57) ABSTRACT

Provided is an implant for restoring the mobility of an articular end of a bone. The implant includes a framework having a first face and a second face opposite the first face, the framework is defined by a plurality of free volumes formed by a grating, where the grating includes a first series of bars extending through the framework from the first face to the second face, and a second series of bars extending through the framework from the first face to the second face, wherein the second series of bars are parallel to one another, and spaced apart in pairs, where the bars have ends along the second face that are bevelled.

20 Claims, 1 Drawing Sheet

Figure 1:
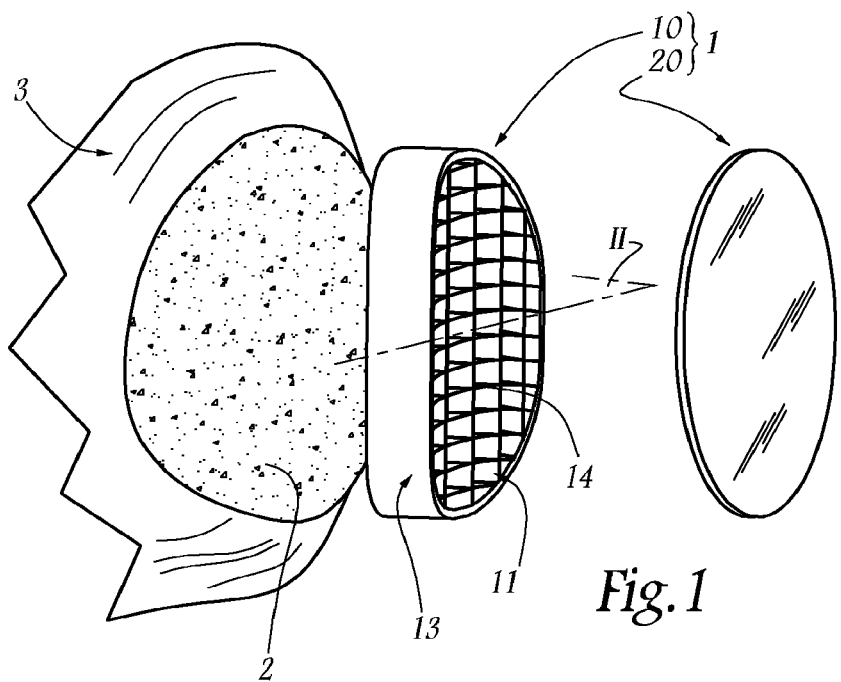

Related U.S. Application Data continuation of application No. 13/148,664, filed as application No. PCT/EP2010/051539 on Feb. 9, 2010, now Pat. No. 10,105,229.

(60) Provisional application No. 61/151,354, filed on Feb. 10, 2009.

(52) U.S. Cl.
CPC ............ *A61F 2002/30014* (2013.01); *A61F 2002/30062* (2013.01); *A61F 2002/30227* (2013.01); *A61F 2002/30433* (2013.01); *A61F 2002/30448* (2013.01); *A61F 2002/30461* (2013.01); *A61F 2002/30462* (2013.01); *A61F 2002/30766* (2013.01); *A61F 2002/30884* (2013.01); *A61F 2002/30911* (2013.01); *A61F 2002/3092* (2013.01); *A61F 2002/4681* (2013.01); *A61F 2210/0004* (2013.01); *A61F 2220/0041* (2013.01); *A61F 2220/005* (2013.01); *A61F 2220/0075* (2013.01); *A61F 2230/0069* (2013.01); *A61F 2250/0018* (2013.01); *A61F 2310/00011* (2013.01); *A61F 2310/00353* (2013.01); *A61F 2310/00365* (2013.01)

(58) Field of Classification Search
CPC .. A61F 2002/30761; A61F 2002/30766; A61F 2002/30751
See application file for complete search history.

(56) References Cited

U.S. PATENT DOCUMENTS

| | | |
|---|---|---|
| 2001/0039455 A1 | 11/2001 | Simon et al. |
| 2002/0173855 A1 | 11/2002 | Mansmann |
| 2002/0183845 A1 | 12/2002 | Mansmann |
| 2003/0225459 A1 | 12/2003 | Hammer et al. |
| 2004/0199250 A1 | 10/2004 | Fell |
| 2004/0236424 A1 | 11/2004 | Berez et al. |
| 2006/0094112 A1 | 5/2006 | Babalola et al. |
| 2006/0235542 A1 | 10/2006 | Hodorek et al. |
| 2009/0105772 A1 | 4/2009 | Seebeck et al. |
| 2009/0157194 A1 | 6/2009 | Shikinami |
| 2010/0016981 A1 | 1/2010 | Roger |
| 2010/0145451 A1 | 6/2010 | Dee |
| 2013/0211534 A1* | 8/2013 | Taylor ................. A61F 2/30771 264/319 |

* cited by examiner

IMPLANT FOR BONE AND CARTILAGE RECONSTRUCTION

The present invention relates to an implant for bone and cartilage reconstruction.

The invention concerns the treatment of the articular ends of the human bones. These bone ends can suffer osteochondral damage related to ageing, to disease, to an accident and/or to a previous surgical intervention. To treat this damage, bone grafts are often implanted that return the treated bone end to its initial volume, without in so doing restoring the original articular cartilage. Unless a mechanical joint prosthesis is fitted, implantation of a graft allows the patient to recover only a small degree of mobility in the area of the damaged joint, or indeed no mobility at all if arthrodesis is performed.

The aim of the present invention is to make available a reconstruction implant with which it is possible to restore the mobility of an articular end of a bone of a patient.

With this aim in mind, the subject matter of the invention is an implant for bone and cartilage reconstruction, characterized in that it comprises a grated framework and a sheet made of a biological tissue material, this sheet firmly covering a first face of the framework, while a second face of the framework, opposite the first face, is designed to be pressed rigidly against, and firmly joined to, an articular end of a bone of a patient.

The invention is based on the concept of making available a refined implant structure whose framework, which is akin to a grating, can be fixed firmly against the articular end of a bone to be treated, with a view to being gradually colonized by regrowth of bone between the constituent elements of this grating, while a layer of cartilage forms again in the area of the sheet of tissue. The implant according to the invention thus forms, in one piece, an osteochondral structure that is able to treat extensive damage of the articular end of a bone, by restoring the mobility of this bone end. The reconstruction of both bone and cartilage achieved by the implant according to the invention is effective and lasting.

According to other advantageous features of the implant of the invention, taken either separately or in all the technically possible combinations:

the second face of the framework is designed to be driven into the end of the bone;
the grating of the framework is designed, in the area of the second face of the framework, to engage by pressure in the osseous substance constituting the end of the bone;
the second face of the framework is provided with at least one element which juts out from the rest of the second face and which is designed to fit in a substantially matching cavity delimited within the end of the bone;
the sheet is bound firmly to the first face of the framework by attached mechanical means;
the mechanical means are chosen from among at least one screw, at least one staple, at least one clip, at least one flange, at least one stitch, at least one adhesive, and several thereof, these means preferably being bioresorbable;
the grating area of the of the framework, especially in the first face of the framework, is made of a porous osseointegration material;
the grating of the framework, especially in the area of the second face of the framework, is made of a material chosen from among a bioresorbable polymer, a non-resorbable polymer, a metal alloy, collagen, and a mixture of several of these;
the implant additionally comprises a filler substance for partially or completely filling the free volumes of the grating of the framework;
the filler substance is chosen from among a cement, preferably biological cement, a solution containing bone growth factor and/or cartilage growth factor, a bone graft, and a mixture of several of these.

Figure 2:
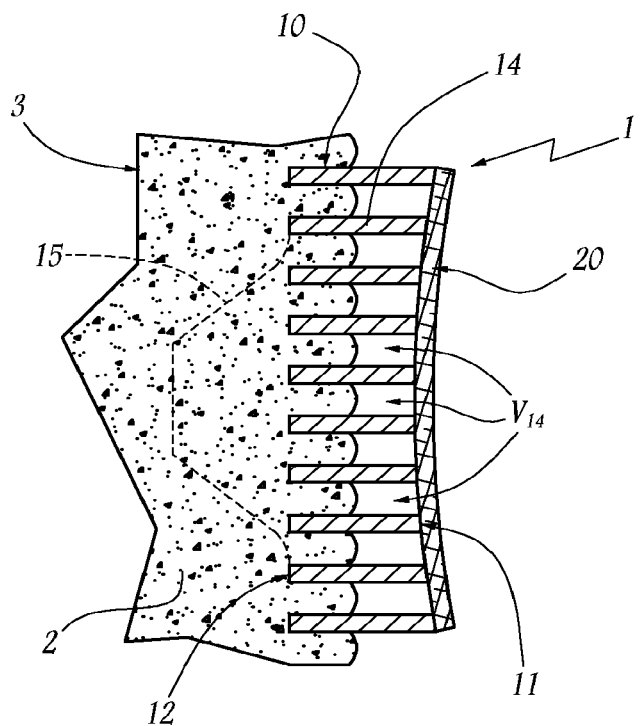

The invention will be better understood from the following description which is given solely by way of example and with reference to the drawings, in which:

FIG. 1 is a perspective schematic view of an implant according to the invention, shown in an exploded form and in association with an articular end of a bone that is to be treated; and FIG. 2 is a cross section, in the plane II, of the implant from FIG. 1, in an assembled state and after implantation in the bone.

FIGS. 1 and 2 show a reconstruction implant 1 designed to replace an osteochondral part of the articular end 2 of a bone 3 of a patient being operated on, which osteochondral part is damaged, destroyed or absent or has been previously removed by surgery. In practice, the reconstruction implant 1 can be used on human bones whose ends are connected by various joints, for example the joints of the ankle, elbow, shoulder, hip and knee.

The reconstruction implant 1 principally comprises, or exclusively comprises as in the embodiment shown here, a framework 10 and a sheet 20, which are rigid and flexible, respectively, compared to each other.

The framework 10 has a three-dimensional overall shape, here a disc-like shape, which delimits two opposite main faces 11 and 12. During use, the face 11 is oriented away from, and the face 12 oriented towards, the end 2 of the bone 3. In the embodiment shown in the figures, the faces 11 and 12 are connected to each other, along the outer periphery of the framework 10, by a peripheral face 13.

As can be clearly seen in FIG. 1, the framework 10 is composed of a grating 14, here in the form of a rigid assembly of bars spaced apart from one another. Thus, in this embodiment, the bars of the grating 14 are distributed in a first series of bars, parallel to one 25 another and spaced apart in pairs, and a second series of bars, parallel to one another, spaced apart in pairs and perpendicular to the bars of the first series.

Free volumes $V_{14}$ are delimited between the bars of the grating 14 and open out both on the face 11 and also on the face 12 of the framework 10, as can be clearly seen in FIG. 2.

The grating 14 is designed and dimensioned to give the framework 10 substantial mechanical strength, in the sense that the framework is then able, on the one hand, to withstand, without damage, external stresses of an intensity at least equal to or even greater than the intensity of the stresses normally applied from the anatomical point of view to the end 2 of the bone 3, and, on the other hand, to be pressed firmly against the end 2 of the bone 3 so as to be joined firmly thereto. In the embodiment shown in the figures, this mechanical strength of the grating 14 is afforded by the rigid assembly of its bars, it being noted that a certain degree of flexibility of this assembly may be tolerated, or indeed desired, in the area of the face 11 of the framework 10, whereas, in the area of the opposite face 12, the rigidity and mechanical stability of the grating 14 are essential.

The mechanical strength of the framework 10, especially in the area of its face 12, is advantageously such that the latter can be anchored by being driven into the osseous substance constituting the end 2 of the bone 3. Thus, as is shown in FIG. 2, the grating 14 is able to be engaged by pressure in the end 2 of the bone 3 without suffering damage, and osseous substance originating from this bone end then engages in each of the free volumes $V_{14}$, in particular in the area where these free volumes open out on the face 12 of the framework 10. For this purpose, the ends of the bars of the grating 14, in the area of the face 12, can advantageously be bevelled, pointed, etc.

In practice, the material constituting the grating 14, especially in the end part of the bars situated towards the face 12 of the framework 10, must have a certain degree of mechanical strength. By way of example, this material is chosen from among a non-resorbable polymer, a bioresorbable polymer, a metal alloy, collagen, etc., and, if appropriate, a mixture of several of the aforementioned materials.

As an optional arrangement aimed at reinforcing the connection of the framework 10 to the end 2 of the bone 3, the face 12 is provided with one or more elements which jut out from the rest of the face 12, one such protruding element being symbolized simply by broken lines in FIG. 2 and labelled by reference sign 15. Said protruding element or elements are designed to fit in a substantially matching cavity that has been formed beforehand in the end 2 of the bone 3. In practice, said protruding element or elements thus correspond to pins, pegs, broaches, etc.

When the reconstruction implant 1 is in the assembled state for use, the face 11 of the framework 10 is covered, at least partially, by the sheet 20, as is shown in FIG. 2.

The sheet 20 is fixed against the face 11 by any suitable means, preferably by attached mechanical means, advantageously bioresorbable mechanical means, not shown in the figures. By way of example, screws and/or staples are passed through the sheet 20 and anchored in the grating 14 of the framework 10. Alternatively, clips wedge the sheet 20 against the face 11. Another possibility is one in which, when the sheet 20 is placed against the face 11 of the framework 10, it protrudes all the way round from said face, such that a flange can be attached in order to press the peripheral circumference of the sheet against the peripheral face 13 of the framework. Such a flange can also be used to additionally strengthen the rigidity of the framework 10 in the area of the face 12 thereof. Moreover, an adhesive, preferably biological adhesive, can be interposed between the sheet 20 and the face 11 of the framework 10. Likewise, the sheet 20 can be stitched directly onto the grating 14 with the aid of suture threads.

In all cases, the sheet 20 forms a flexible layer on the face 11 of the framework 10, making it possible to restore a cartilaginous thickness against which that bone connected to the bone 3 by the surgically modified joint will be able to articulate. For this purpose, the face 11 of the framework 10 is advantageously concave, as in the figures, or convex, with the sheet 20 then matching the curvature of the face 11 in order to restore a correspondingly shaped articular layer of cartilage, as is shown in FIG. 2.

In practice, the sheet 20 is made of a biological tissue material, especially a tissue matrix of animal origin, in particular of porcine origin or human origin, or a synthetic one.

To facilitate the colonization of the reconstruction implant 1 by bone and cartilage, the grating 14, especially in the end part of its bars directed towards the face 11, is made of a porous osseointegration material.

The use of the reconstruction implant 1 is simple. Prior to this actual use, the framework 10 and the sheet 20 are joined firmly to each other preoperatively, preferably followed by sterilization, or during surgery. After the soft tissue parts have been freed from around the end 2 of the bone 3, and, if appropriate, after this bone end has been prepared, for example by resection, the surgeon manoeuvres the framework 10 in such a way as to press the face 12 thereof rigidly against the end 2 of the bone 3, until it is joined firmly thereto. The stability of this join is remarkable.

Thereafter, the implant 1 will gradually be colonized, on the one hand by bone substance from the end 2 of the bone 3 advancing inside the free volumes $V_{14}$, and on the other hand by cartilaginous substance within the sheet 20. After a certain time, the implant 1 thus restores the osteochondral structure of the bone 3.

If appropriate, during implantation of the framework 10 in the end 2 of the bone 3, the surgeon can partially or completely fill the inside of the free volumes $V_{14}$ with a specific substance, especially by injecting this substance. It will be appreciated that this substance does not participate significantly in the primary fixation of the implant 1, which is ensured essentially by the face 12 of the framework 10, but may promote the colonization of the implant by bone and cartilage, thus reinforcing the secondary fixation of the implant.

By way of example, the aforementioned filler substance can be a cement, preferably biological cement, a solution containing bone and cartilage growth factors, a bone graft in the form of a "paste", etc.

What is claimed is:

1. An implant comprising:
   a framework having a first face and a second face opposite the first face, the framework defined by a plurality of free volumes formed by a grating,
      wherein the plurality of free volumes extends entirely through the framework from the first face to the second face with a similar cross-sectional dimension from the first face to the second face, wherein the grating comprises:
         a first series of bars extending through the framework from the first face to the second face, wherein the first series of bars are parallel to one another, and spaced apart in pairs; and
         a second series of bars extending through the framework from the first face to the second face, wherein the second series of bars are parallel to one another, and spaced apart in pairs,
      wherein the bars have ends along the second face that are beveled such that a difference in the cross-sectional dimensional of the plurality of free volumes from the first face to the second face is due to the beveling,
      wherein the second face of the framework lies in a same plane;
      wherein the second face is configured to be pressed rigidly against and firmly joined to a bone; and
      wherein the plurality of free volumes is configured to be partially or completely filled;
   a flexible member positioned along the first face of the framework, wherein the flexible member abuts and firmly covers the plurality of free volumes, wherein the framework is more rigid than the flexible member; and
   a protruding element extending from the framework in a direction away from the first face, wherein the protruding element is configured to reinforce a connection of the framework to the bone.

2. The implant of claim 1, wherein the framework comprises a metal alloy.

3. The implant of claim 1, wherein the framework comprises a polymer.

4. The implant of claim 1, wherein the framework is configured to promote osseointegration.

5. The implant of claim 1, wherein the entire first face of the framework comprises a concave shape.

6. The implant of claim 1, wherein the flexible member is convex when coupled to the framework.

7. The implant of claim 1, wherein the flexible member comprises a synthetic material.

8. The implant of claim 1, wherein the flexible member is joined with the framework pre-operatively.

9. The implant of claim 1, wherein the flexible member is configured to restore a cartilaginous thickness against which another bone is configured to articulate.

10. An implant comprising:
a frame having a first surface and a second surface opposite the first surface, the frame comprising a plurality of openings therethrough formed by a grating, the plurality of openings extending entirely through the frame from the first surface to the second surface and within a periphery of the frame, wherein each opening forms a continuous through lumen from the first surface to the second surface, wherein the second surface lies along a plane;
wherein, during use, the second surface is configured to be positioned adjacent to a bone;
wherein the grating comprises:
a first series of bars, parallel to one another, and spaced apart in pairs; and
a second series of bars, parallel to one another, and spaced apart in pairs,
wherein the bars have ends along the second face that are bevelled,
wherein the second face of the frame lies in a same plane;
wherein the second face is configured to be pressed rigidly against and firmly joined to the bone; and
wherein the plurality of openings is configured to be partially or completely filled;
a flexible member fixed directly to the first surface of the frame to cover the first surface of the frame, wherein the frame is more rigid than the flexible member, wherein the entire first surface of the frame is concave, wherein the implant is designed to replace the entire articular end of the bone of a patient; and
a protruding element extending from the frame and configured to facilitate anchoring of the implant to the bone.

11. The implant of claim 10, wherein the frame comprises a metal alloy or a polymer.

12. The implant of claim 10, wherein the frame is configured to promote osseointegration.

13. The implant of claim 10, wherein the flexible member comprises a synthetic material.

14. The implant of claim 10, wherein the flexible member is configured to restore a cartilaginous thickness against which another bone articulates.

15. The implant of claim 10, wherein the flexible member is configured to restore a corresponding shaped articular layer of cartilage.

16. An implant comprising:
a framework having a first proximal face, a second distal face and an outer periphery, wherein a plurality of free volumes are defined by a grating between the proximal first face and the second distal face, wherein the second distal face is configured to be positioned adjacent to a bone and second distal face is planar, wherein each free volume is entirely enclosed by the framework from the first proximal face to the second distal face, wherein each free volume extends entirely through the framework;
wherein the grating comprises:
a first series of bars, parallel to one another, and spaced apart in pairs; and
a second series of bars, parallel to one another, and spaced apart in pairs,
wherein the bars have ends along the second face that are bevelled;
a means for restoring a cartilaginous thickness of a joint, the means for restoring the cartilaginous thickness of the joint being secured to the framework pre-operatively, wherein the framework is more right than the means for restoring the cartilaginous thickness of the joint; and
a protruding element extending distally from the framework and configured to reinforce a connection of the framework to the bone, wherein the protruding element does not extend laterally beyond the outer periphery of the framework.

17. The implant of claim 16, wherein the means for restoring the cartilaginous thickness of the joint comprises a flexible layer.

18. The implant of claim 16, wherein the means for restoring the cartilaginous thickness of the joint comprises a synthetic material having a thickness.

19. The implant of claim 16, wherein the framework comprises a metal alloy or a polymer.

20. The implant of claim 16, wherein the protruding element comprises a peg.

* * * * *